US008037762B2

(12) United States Patent
La Rosa Flores et al.

(10) Patent No.: US 8,037,762 B2
(45) Date of Patent: Oct. 18, 2011

(54) WHISPERING GALLERY MODE ULTRASONICALLY COUPLED SCANNING PROBE MICROSCOPY

(75) Inventors: Andres H. La Rosa Flores, Beaverton, OR (US); Richard Nordstrom, Hillsboro, OR (US); Sudhaprasanna Kumar Padigi, Portland, OR (US)

(73) Assignee: State of Oregon Acting by and through The State Board of Higher Education on Behalf of Portland State University, Portland, OR (US)

( * ) Notice: Subject to any disclaimer, the term of this patent is extended or adjusted under 35 U.S.C. 154(b) by 672 days.

(21) Appl. No.: 11/809,196

(22) Filed: May 30, 2007

(65) Prior Publication Data
US 2008/0092659 A1   Apr. 24, 2008

Related U.S. Application Data

(63) Continuation-in-part of application No. 11/384,088, filed on Mar. 17, 2006.

(60) Provisional application No. 60/663,557, filed on Mar. 18, 2005, provisional application No. 60/809,541, filed on May 30, 2006.

(51) Int. Cl.
*G01N 29/06* (2006.01)

(52) U.S. Cl. ................. 73/606; 73/618; 73/607

(58) Field of Classification Search ............ 73/618, 73/620, 105, 606, 627, 607
See application file for complete search history.

(56) References Cited

U.S. PATENT DOCUMENTS

| 4,469,554 A | 9/1984 | Turner |
| 4,646,573 A | 3/1987 | Stoll |
| 5,172,002 A | 12/1992 | Marshall |
| 5,200,616 A * | 4/1993 | Kokawa et al. ............... 850/14 |
| 5,319,977 A | 6/1994 | Quate et al. |
| 5,760,396 A * | 6/1998 | Lindsay et al. ............... 850/1 |
| 5,852,233 A | 12/1998 | Arnold et al. |
| 5,886,532 A | 3/1999 | Hsu et al. |
| 6,094,971 A | 8/2000 | Edwards et al. |
| 6,981,417 B1 * | 1/2006 | Oravecz ............... 73/619 |
| 2005/0092907 A1 | 5/2005 | West et al. |
| 2006/0037401 A1 | 2/2006 | Shekhawat et al. |
| 2006/0152232 A1 | 7/2006 | Shvets et al. |
| 2008/0276695 A1 * | 11/2008 | Prater et al. ............... 73/105 |

OTHER PUBLICATIONS

Stöckle et al., "High-quality near-field optical probes by tube etching," *Appl. Phys. Lett.* 75:160-162 (1999).
La Rosa et al., "The ultrasonic/shear-force microscope: integrating ultrasonic sensing into a near-field scanning optical microscope," *Rev. Sci. Instrum.* 76:093707-1 (2005).
La Rosa et al., "The Shear-force/Ultrasonic Near-field Microscope: A Nanometrology Tool for Surface Science and Technology," *Proc. SPIE*, vol. SA111 (2005).

(Continued)

*Primary Examiner* — Hezron Williams
*Assistant Examiner* — Nashimiya Fayyaz
(74) *Attorney, Agent, or Firm* — Klarquist Sparkman, LLP

(57) ABSTRACT

Scanning probe microscopes include a probe tip coupled to a tuning fork or other acoustic resonator so as to apply a shear force when contacted to a specimen surface based on an applied acoustic signal. A secondary ultrasonic transducer is in acoustic communication with the specimen and a resonant structure. Probe tip-specimen displacement can be detected based on whispering gallery mode ultrasonic waves in the resonant structure using the secondary transducer, and such displacements maintained using feedback control based on whispering gallery mode acoustic wave magnitude.

10 Claims, 14 Drawing Sheets

OTHER PUBLICATIONS

Cui, et al., "Investigation of the probe-sample interaction in the ultrasonic/shear-force microscope: The phononic friction mechanism," Appl. Phys. Lett. 87:231907 (2005).

Karrai and Tiemann, "Interfacial Shear Force Microscopy," *Phys. Rev. B* 62:13174 (2000).

* cited by examiner

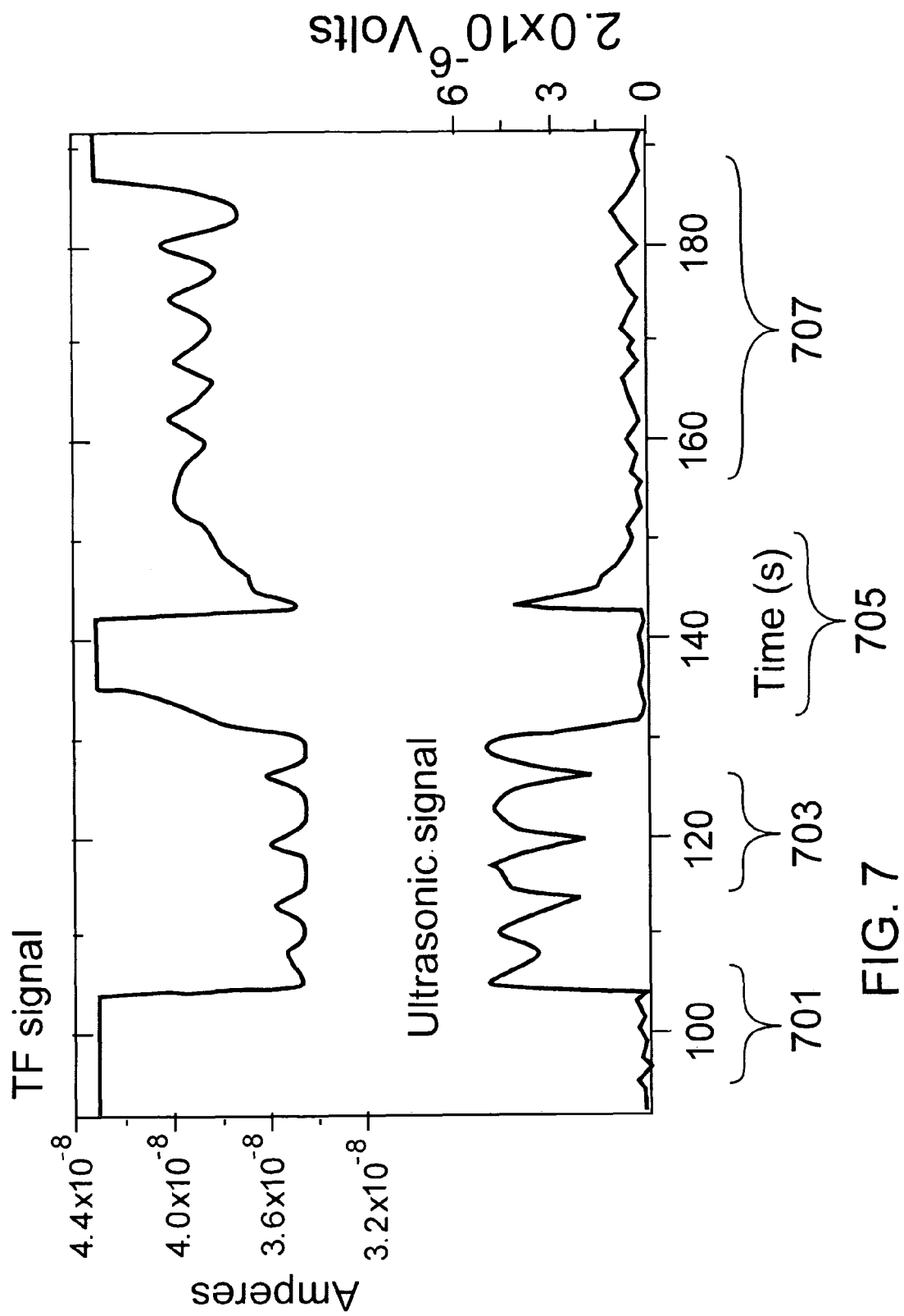

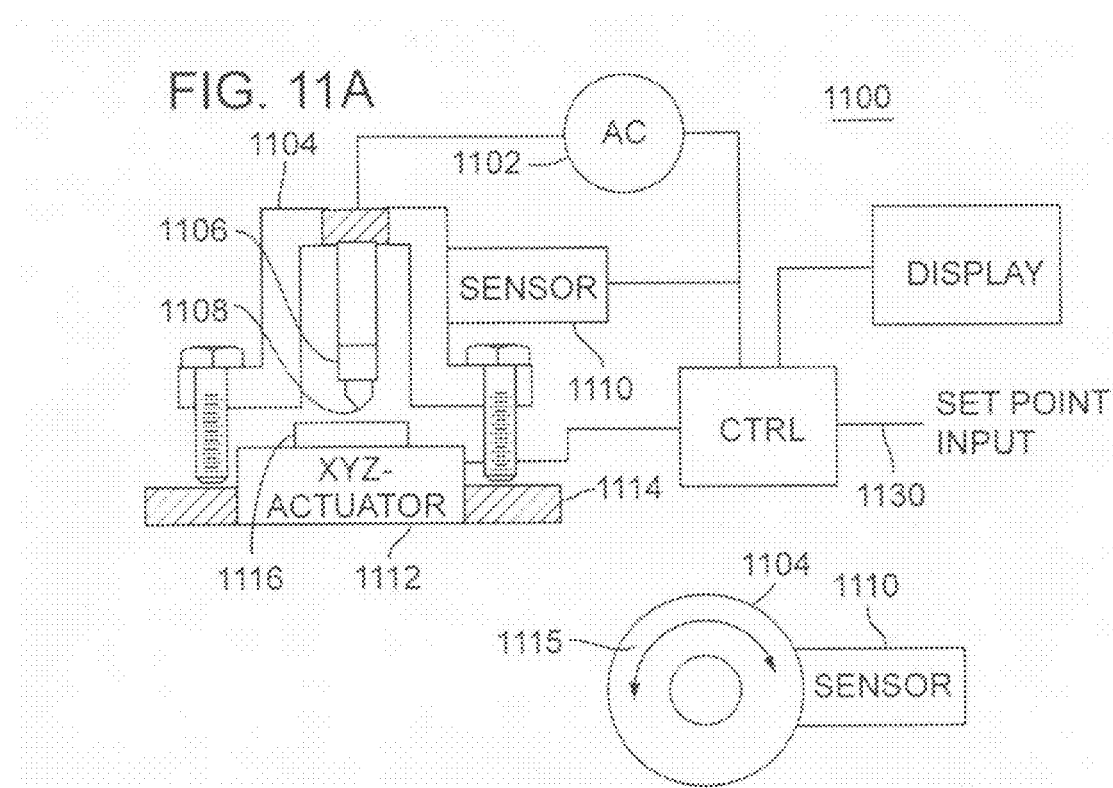
FIG. 11A
FIG. 11B
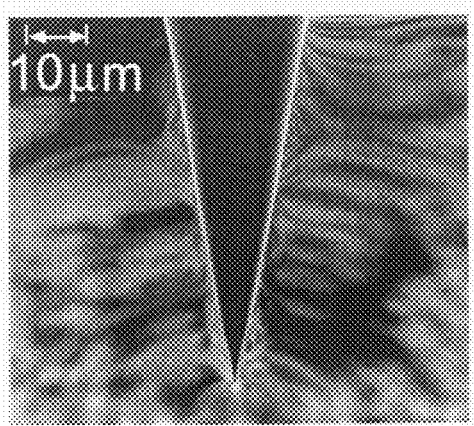
FIG. 12

WHISPERING GALLERY MODE ULTRASONICALLY COUPLED SCANNING PROBE MICROSCOPY

CROSS REFERENCE TO RELATED APPLICATIONS

This application claims priority from U.S. Provisional Patent Application No. 60/809,541, filed May 30, 2006, and is a continuation-in-part of U.S. Patent Application 11/384,088, filed Mar.17, 2006, which claims priority from U.S. Provisional Patent Application No. 60/663,557, filed Mar.18, 2005.

FIELD

The disclosure pertains to scanning probe microscopes.

BACKGROUND

Scanning probe microscopes can be used for high resolution sample measurements. The lateral resolution of conventional optical microscopes is generally limited by diffraction effects, while in scanning probe microscope the resolution is limited by the dimensions of the scanning probe tip which is typically between about 5 nm and 100 nm. Some customary scanning probe microscopes include the atomic force microscope (AFM) and the near-field scanning optical microscope (NSOM). The AFM measures surface topographies by detecting a force exerted on a probe. In one configuration, a probe is secured to a cantilever, and deflections of the cantilever are estimated using laser beam illumination of the cantilever. The NSOM uses a probe having a small illumination aperture through which optical radiation is directed to a sample; and can be used to measure topographic and optical properties.

The AFM has been used to study frictional forces. A probe tip is dragged along a specimen surface and its lateral bending is monitored. This lateral bending is caused by frictional forces between the probe and the specimen. The smaller the bending experienced by the probe, the lower the frictional force. While such AFM-based measurements can provide useful insights into surface interactions, these measurements have significant limitations. For example, AFM-based measurements are associated only with frictional forces on the AFM probe, but provide no information on any effects on the sample, such as how energy is transferred to the sample by the probe. AFM-based measurements also provide limited information on any probe interactions with thin adsorbed fluid layers on specimen surfaces. Accordingly, methods and apparatus are needed that can provide enhanced specimen characterizations.

SUMMARY

Scanning microscopes comprise a probe having a probe tip for contacting a specimen and a probe stage configured to move the probe tip toward the specimen. A first acoustic transducer is coupled to the probe or a probe mount and a second acoustic transducer is adapted to be acoustically coupled to the specimen. In some examples, a first transducer driver is configured to produce an acoustic vibration of the probe tip with the first acoustic transducer, and a first transducer detector is situated to receive an electrical signal produced by the second acoustic transducer in response to the acoustic vibration of the probe tip. In further examples, a translation stage is configured for scanning the probe tip with respect to a specimen surface, and an image processor is configured to receive electrical signals from the first transducer detector as the probe tip is scanned to produce an image of a specimen surface. In some particular examples, a quartz tuning fork includes the first acoustic transducer, wherein the probe tip is secured to a tine of the tuning fork. In additional examples, the first transducer detector is configured to detect probe tip vibration based on an assessment of a tuning fork vibration amplitude or resonance frequency shift. In other alternatives, the first transducer detector is configured to detect probe tip vibration based on an assessment of a tuning fork admittance or based on an assessment of a frequency associated with a maximum amplitude of a tuning fork vibration. In some examples, the first transducer detector is configured to detect a resonance frequency shift or other property of a probe tip oscillation, and an admittance can be estimated based on such oscillation properties.

In still further examples, a first transducer driver is configured to produce an acoustic vibration of the specimen with the second acoustic transducer, and a first transducer detector is situated to receive an electrical signal produced by the first acoustic transducer in response to the acoustic vibration of the specimen. In some examples, a translation stage is configured for scanning the probe tip with respect to a specimen surface, and an image processor is configured to receive electrical signals from the first transducer detector as the probe tip is scanned to produce an image of a specimen surface. In other representative embodiments, a quartz tuning fork includes the first acoustic transducer, wherein the probe tip is secured to a tine of the tuning fork, and the first transducer detector is configured to detect probe tip vibration based on an assessment of a tuning fork vibration amplitude, a tuning fork admittance, or a frequency or frequency shift associated with a maximum amplitude of a tuning fork vibration.

Methods comprise scanning a probe tip over a specimen surface and applying an acoustic signal to the specimen. The acoustic signal is coupled between the specimen and the probe tip, and the coupled acoustic signal is detected. An image is formed based on the detected coupled acoustic signal. In other examples, the acoustic signal is applied to the specimen with a transducer that is secured to the probe tip or the coupled acoustic signal is detected with an acoustic transducer that is secured to the probe tip. In other examples, the acoustic signal is applied to the specimen with a transducer that is secured to the specimen.

In other methods, an acoustic signal is applied to a probe tip and a probe tip distance from a specimen surface is estimated based on detecting an acoustic signal at the specimen. In a representative examples the method includes establishing that a probe tip oscillation remains substantially unchanged at the distance at which the acoustic signal from the specimen is detected.

Scanning probe microscopes comprise a probe having a probe tip for contacting a specimen and a stage configured to provide a selected probe tip-specimen displacement. A first acoustic transducer is coupled to the probe, and a second acoustic transducer is coupled to a resonant cavity that is acoustically coupled to the probe tip. The second acoustic transducer is situated to detect acoustic waves in the resonant cavity. In some examples, a first transducer driver is configured to produce an acoustic vibration of the probe tip with the first acoustic transducer at a probe tip frequency, wherein the resonant cavity dimensions are based on the probe tip frequency. In other examples, a translation stage is configured for scanning that the probe tip with respect to a specimen surface, and an image processor is configured to receive electrical signals from the second transducer associated with acoustic waves in the resonant cavity as the probe tip is scanned and to produce an image of a specimen surface based on the received electrical signals. In additional examples, a controller is configured to adjust probe tip-specimen separation to maintain a predetermined acoustic wave magnitude in the resonant cavity and a display is configured to present a specimen image based on the adjusted probe tip-specimen separations.

Methods comprising scanning an oscillating probe tip over a specimen surface and coupling an acoustic vibration associated with oscillations of the probe tip to a resonant cavity so as to form a resonant acoustic wave. Probe tip-specimen separation is estimated based on the resonant acoustic wave. In some examples, the probe tip is scanned with respect to the specimen surface and the probe tip-specimen surface separation is adjusted so as to maintain a predetermined resonant acoustic wave characteristic such as acoustic wave amplitude. In other examples, a specimen image is based stored displacement adjustments.

The foregoing and other features and advantages of the disclosed technology will become more apparent from the following detailed description, which proceeds with reference to the accompanying figures.

BRIEF DESCRIPTION OF THE DRAWINGS

FIG. 7 is a graph illustrating shear force and ultrasonic signal amplitudes as a function of probe-specimen displacement.

FIGS. 11A-11B are schematic diagrams of a WGRUS based scanning microscope configured to control tip-sample vertical distance (z) based on detection of whispering-gallery ultrasonic waves.

FIG. 12 is an electron micrograph of a typical tapered fiber probe used in the WGRUS scanning microscope of FIGS. 11A-11B.

DETAILED DESCRIPTION

As used in this application and in the claims, the singular forms "a," "an," and "the" include the plural forms unless the context clearly dictates otherwise. Additionally, the term "includes" means "comprises." Further, the term "coupled" means electrically, electromagnetically, or acoustically connected or linked and does not exclude the presence of intermediate elements between the coupled items.

The described systems, apparatus, and methods described herein should not be construed as limiting in any way. Instead, the present disclosure is directed toward all novel and non-obvious features and aspects of the various disclosed embodiments, alone and in various combinations and sub-combinations with one another. The disclosed systems, methods, and apparatus are not limited to any specific aspect or feature or combinations thereof, nor do the disclosed systems, methods, and apparatus require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed systems, methods, and apparatus can be used in conjunction with other systems, methods, and apparatus. Additionally, the description sometimes uses terms like "produce" and "provide" to describe the disclosed methods. These terms are high-level abstractions of the actual operations that are performed. The actual operations that correspond to these terms will vary depending on the particular implementation and are readily discernible by one of ordinary skill in the art.

Representative methods and apparatus are described herein that are associated with scanning probe microscopes. In one representative example, a so-called Ultrasonic/Shear-Force Microscope (USFM) is described which can be used as, for example, an analytical tool to investigate the dynamics displayed by fluid-like films when subjected to mesoscopic confinement. In the disclosed examples, one or more acoustic transducers can be provided to apply or detect acoustic signals on a specimen. In some examples disclosed herein, ultrasonic signals are applied or detected. For convenience, acoustic signals having a frequency of at least about 20 kHz are referred to as ultrasonic, while acoustic signals having frequencies greater than about 10 Hz can be used.

Figure 1:
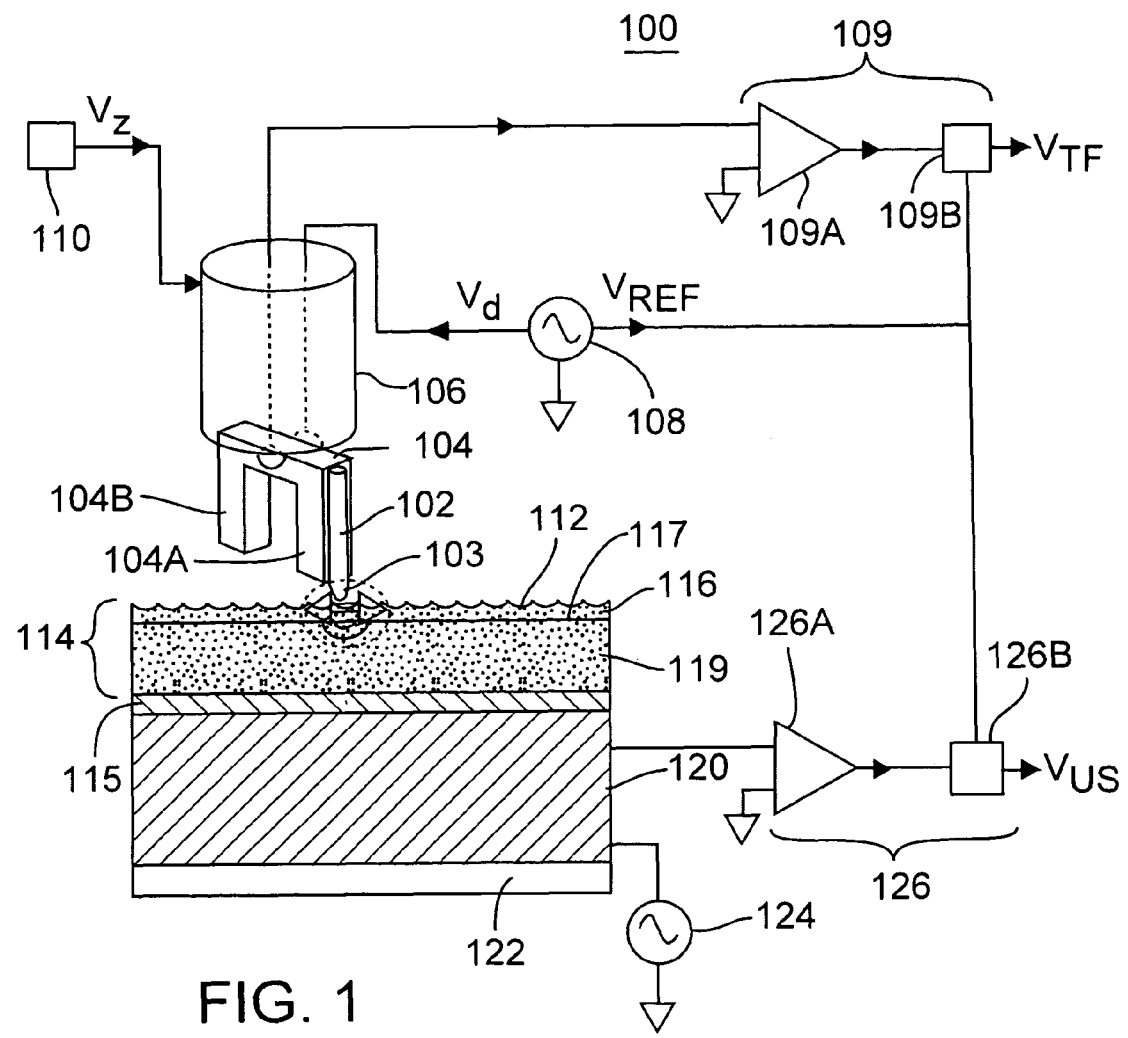
FIG. 1 is a schematic diagram of a scanning probe microscope that includes an ultrasonic sensor.

Referring to FIG. 1, a representative USFM 100 includes a probe 102 coupled to a quartz tuning fork 104 and a piezoelectric stage 106. The quartz tuning fork 104 includes first and second tines 104A, 104B and is configured to oscillate at a selected frequency, typically between about 1 kHz and 500 kHz and can have a quality factor (Q) of between about 1,000 and 50,000. The tuning fork 104 is electrically coupled to tuning fork driver 108 and to a detection system 109 that includes a preamplifier 109A and a lock-in amplifier 109B. The tuning fork driver 108 is generally configured to provide an electrical signal to the tuning fork 104 so that displacements of the tines 104A, 104B are in range of up to about 1-50 nm, but tine displacements of about 1-10 nm are convenient.

A stage controller 110 is configured to supply an electrical signal to the piezoelectric stage 106 to control the vertical displacement of a probe tip 103 from a specimen 114. In some examples, the piezoelectric stage controller 110 uses a feedback-based control scheme to compensate piezoelectric stage properties such as stage hysteresis for accurate and repeatable probe tip placement. As shown in FIG. 1, vertical displacements are associate with probe-specimen separations, while translations in a horizontal plane can be used in scanning to obtain specimen images. This arrangement is used for convenience, and other orientations can be used.

As shown in FIG. 1, a specimen 114 includes an adsorbed fluid layer 116 that defines a specimen surface 112. This adsorbed fluid layer 116 can also be referred to as a contaminant layer, and generally the probe 102 contacts a surface such as the surface 112 prior to contacting a surface 117 of an underlying specimen body 19. The surface 117 can also be referred to as a solid surface as it is the surface of the (usually) solid specimen 114. The specimen 114 is in contact with an ultrasonic transducer 120 via an acoustic coupling medium 115 and is supported by a specimen stage 122. The ultrasonic transducer 120 can be coupled to an ultrasonic signal generator 124 and an ultrasonic signal detector 126 that includes a preamplifier 126A and a lock-in amplifier 126B. The lock-in amplifiers 109B, 126B are both coupled to the tuning fork driver 108 for phase sensitive detection of electrical signals received from the tuning fork 104 and the ultrasonic transducer 120, respectively. Other methods and apparatus can be used as convenient. The specimen stage 122 and/or the piezoelectric stage 106 are generally secured to a two-axis scanning stage so that the probe tip 103 can be laterally scanned over the specimen surface 112. A tuning fork signal $V_{TF}$ and/or an ultrasonic sensor signal $V_{US}$ can be acquired during scanning, and processed to form images.

In operation, the tuning fork (TF) 104 is activated by the driver 108 and is moved towards the specimen surface 117 until an interaction of the probe tip 103 with the specimen 114 is detected. Typically, a probe/specimen interaction is detected based on a decrease in amplitude and a shift in the resonant frequency of the tuning fork 104 determined by detection system 109. Alternatively, a probe/specimen interaction can be detected based on an acoustic signal excited by an ultrasonic sensor and detected at a tuning fork or other acoustic sensor. By scanning the probe tip 103 across the specimen surface 117 and measuring TF resonant frequency shifts or other changes in TF response, a one or two dimensional representation of the surface 117 can be produced. As shown below, the probe tip 103 is also responsive to the layer 1116. An electrical signal associated with the specimen interaction is output by the lock-in amplifier 109B. A shift in a resonance frequency in a tuning fork is a convenient technique for detecting probe/specimen interactions, but other techniques, such as, for example, measurement of laser beam deflection can be used. Because tuning fork based techniques are associated with low power dissipation, they are particularly useful for low temperature operation, but in some examples, probes can be secured to cantilevers instead of tuning forks.

The probe tip 103 can be configured to enhance or select a particular surface interaction. For example, a silicon based probe can be provided with a magnetic tip coating such as, for example, a cobalt alloy coating, for Magnetic Force Microscopy (MFM) or a conductive coating for Scanning Tunneling Microscopy (STM).

The stage ultrasonic transducer 120 can be configured to detect ultrasonic signals propagating in the specimen 114 or specimen stage 122 and associated with interactions of the probe tip 103 and the specimen 114. A detected output signal $V_{US}$ associated with the ultrasonic signal at the specimen or specimen stage is output by the lock-in 126B. This signal can be used to produce a two dimensional image of the specimen 112 in the same manner as a detected frequency shift or change in Q of the tuning fork 104.

In representative examples, a polished silicon wafer is used as the specimen. The probe is a tapered optical fiber (3M fiber FS-SC-6324) fabricated by using a tube etching method which produces a probe tip having a radius of about 30 nm. Such methods are described in, for example, Stöckle et al., "High-quality near-field optical probes by tube etching," Appl. Phys. Lett. 75:160-162 (1999). The probe is attached to a commercially available $2^{15}$ Hz tuning fork which can serve to apply and sense a lateral (shear) force. Because of the additional mass and internal friction associated with attachment of the probe to the tuning fork (typically, the fiber is glued to the tuning fork), the resonant frequency of the tuning fork shifts to a lower frequency. In one example, the resonant frequent shifts to about 31,283 Hz and the tuning fork Q decreases to about $10^3$.

In operation, the TF can be driven by a constant amplitude AC voltage $V_d$ supplied or controlled by the signal generator 108. A constant voltage amplitude TF drive corresponds to a constant force drive. Probe/specimen displacement is controlled using a piezo tube actuator such as an EBL 3 actuator available from Staveley Sensor Inc. Such an actuator has a sensitivity of about 20 nm/V and can be controlled with a variable DC voltage $V_z$. An SE35-Q ultrasonic sensor (available from Dunegan Engineering Consultants, Inc) can serve as the ultrasonic sensor. A layer of vacuum grease can be used between the specimen and the ultrasonic sensor to increase the efficiency of ultrasound transmission. The ultrasonic signal can be detected by the lock-in amplifier 126B. The signal used to drive the tuning fork can be used as a reference signal for the amplifiers 109A, 126A.

As the probe tip approaches the specimen, the resonant frequency and the damping rate (Q) of the tuning fork are changed by conservative and dissipative probe-specimen interactions, respectively. To evaluate the probe-specimen interaction at different heights, the frequency spectrum of the TF admittance is measured using the detection system 109. Using an equivalent electrical circuit model, the resonant frequency and the damping rate change can be estimated by fitting the admittance data as described in, for example, Karrai and Tiemann, "Interfacial shear force microscopy," Phys. Rev. B 62: 13174 (2000).

The motion of TF can be described by the Newton equation:

$$M\ddot{x} = F_{drive} + F_{damp} + F_{restore} = F_{drive} - M\gamma_0\dot{x} - k_0 x, \quad (1)$$

wherein x is the displacement of the TF vibration, $F_{damp}$ is a damping force, $F_{restore}$ is a restoring force due to the TF's elastic deformation, M is an effective mass, $\gamma_0$ is a damping rate of the free TF in air, and $k_0$ is a TF spring constant.

Dissipative and conservative probe-sample interactions and associated forces, $F_{dissipate}$ and $F_{conserve}$, respectively, can contribute to tuning fork motion as follows:

$$M\ddot{x} = F_{drive} + F_{damp} + F_{dissipate} + F_{restore} + F_{conserve} = F_{drive} - M(\gamma_0 + \gamma')\dot{x} - (k_0 + k')x = F_{drive} - M\gamma'\dot{x} - kx \quad (2)$$

wherein $\gamma'$ is an effective damping rate due to the dissipative interaction and k' is a force gradient due to the conservative interaction. The time averaged power dissipated in the velocity dependent dissipative interaction $-M\gamma'x$ is negative, and the time averaged power of the displacement dependent conservative interaction $-k'x$ is zero. $\gamma$ is a total damping rate, and k is a total restoring force gradient.

The electrical response of the TF can be linked to a mechanical response model based on a piezo-electro-mechanical coupling constant $\alpha$ as follows:

$$L\ddot{Q} + R\dot{Q} + \frac{1}{C}Q = V_d, \quad (3)$$

wherein $Q=2\alpha x$, $L=M/2\alpha^2$, $R=M\gamma/2\alpha^2$, $1/C=k/2\alpha^2$, and $V_d=F_{drive}/\alpha$. (Note that Q is also used sometimes herein to refer to resonator quality factor). Because of a parallel capacitance $C_p$ of the TF, an electrical admittance of the TF is:

$$Y(\omega) = \frac{1}{R + i\omega L + \frac{1}{i\omega C}} + i\omega C_p. \quad (4)$$

By fitting measured data to the above model formula, the admittance of the TF and values for L, R, C, $C_p$ can be estimated. In one example, dimensions of the TF tines (length, width, height, respectively) are l=4 mm, t=0.6 mm, and w=0.33 mm, so that $k_{bareTF}=(E/4)w(t/L)^3=22\times10^3$ N/nm. For the bare TF in an ambient environment, C=$1.135\times10^{-14}$ F. Thus, using the equation $1/C=k/2\alpha^2$, the piezo-electro-mechanical coupling constant $\alpha$ of the TF in this example is about $\alpha=11\times10^{-6}$ C/m.

In steady state TF oscillation, the time averaged power consumed by the dissipative probe-sample interaction can be calculated by the mechanical model and the equivalent circuit model separately as $$P_{dissipate} = -\frac{2(F_{drive}^{RMS})^2\gamma'}{M\left[\left(\frac{\omega_0^2}{\omega} - \omega\right)^2 + \gamma^2\right]} = -\frac{(V_d^{RMS})^2(R - R_0)}{L^2\left(\frac{\omega_0^2}{\omega} - \omega\right)^2 + R^2}, \quad (5)$$

wherein $R_0$ is the equivalent resistance of the TF when it is far away from the probe-sample interaction region. The dissipative power has a peak at the resonant frequency $\omega_0^2 k/M = 1/(LC)$. TF driving voltages of about 60 mV, 30 mV, 14 mV, and 6 mV are used, and correspond to drive forces of about 660 nN, 330 nN, 154 nN, and 66 nN, respectively. Approximately the same TF admittance change was obtained for each of these drive voltages.

Figure 2A:
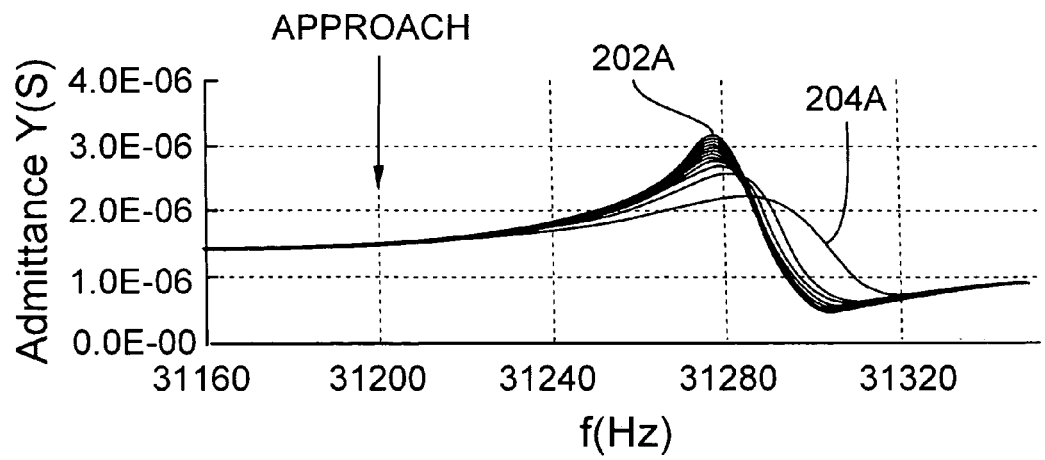
FIG. 2A is a graph of a representative tuning fork admittance spectrum for probe-specimen approach.

FIG. 2A illustrates a TF admittance spectrum at a 60 mV drive voltage with the probe tip moved to approach the specimen. An initial spectrum 202A corresponding to the probe being substantially distant from the specimen changes into a subsequent spectrum 204A as the probe tip approaches the specimen. The closer the probe tip is to the sample, the stronger the probe-sample interaction. The dissipative interaction, corresponding to a damping of the admittance spectrum, increases monotonically. The conservative interaction corresponding to a frequency shift of the admittance spectrum does not change appreciably during the initial movement towards the specimen, but exhibits substantial changes at short probe-sample distances. When the probe tip 103 contacts the sample, the TF admittance curve is distorted. Before contact, the TF admittance curves can be fitted based on the model of Eqn. 4. For this reason, contact is can be identified based on a transition to a distorted TF admittance curve, and the displacement at this transition can be referred to as z=0 nm.

Figure 2B:
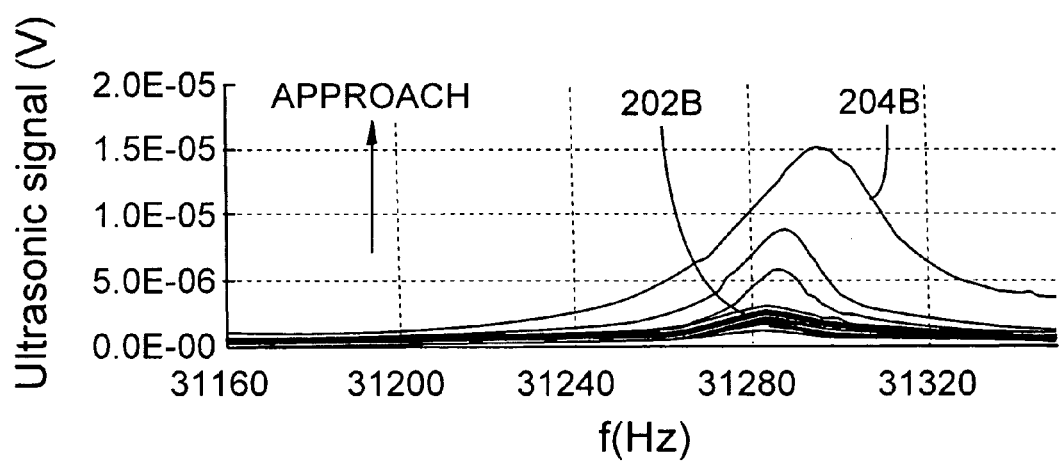
FIG. 2B is a graph of a representative ultrasonic transducer spectrum for probe-specimen approach and corresponding to the tuning fork admittance spectrum of FIG. 2A.
Figure 3:
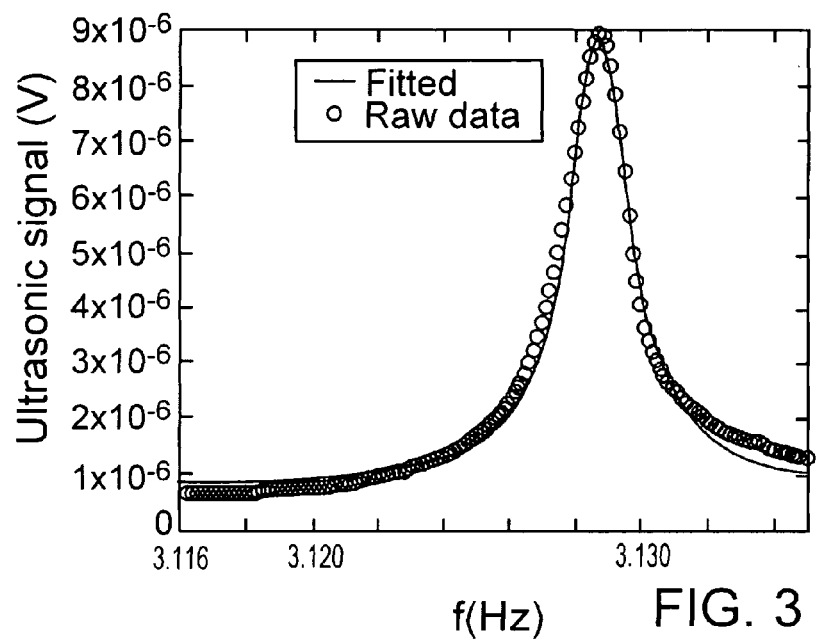
FIG. 3 is a graph illustrating a fit of ultrasonic signal data to a signal model.

FIG. 2B illustrates spectra obtained with the ultrasonic transducer as the probe tip approaches the sample. The spectra of FIG. 2B correspond to those of FIG. 2A and were obtained at the same time with the same 60 mV drive voltage. FIG. 2B illustrates spectra obtained with the ultrasonic transducer as the probe tip approaches the sample. The ultrasonic spectra exhibit similar behavior at different drive voltages, but signal magnitudes depend on drive voltage. Curve fitting of the ultrasonic spectra show that the ultrasonic signal peaks correspond to the TF resonant frequencies $\omega_0=1/\sqrt{LC}$ (which corresponding to the peaks of the TF dissipative power). By choosing a proper scaling factor, the ultrasonic signal can be shown to substantially overlap the TF dissipative power model of Eqn. 5. FIG. 3 is an example of such an overlap for a probe-sample distance $z\approx0.5$ nm.

Figure 4:
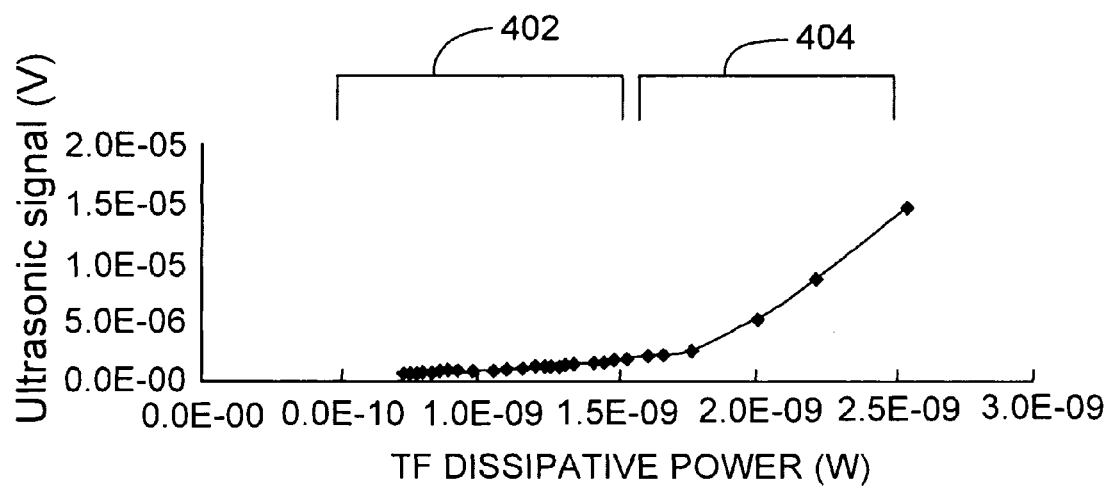
FIG. 4 is a graph illustrating ultrasonic signal magnitude as a function of tuning fork power dissipation.

FIG. 4 illustrates an increasing ultrasonic signal amplitude as a function of increasing TF dissipative power at the resonant frequency as the probe approaches the specimen with the TF drive voltage at 60 mV. Viewing FIG. 4, two distinct regions 402, 404 for ultrasound generation can be observed, with a transition at a probe-specimen separation of about $z\approx1$ nm. When the probe-specimen distance is greater than about 1 nm, ultrasound generation is proportional to TF dissipative power with a first slope. When the probe-sample distance is smaller than about 1 nm, ultrasound generation is also proportional to TF dissipative power but with a second slope that is greater than the first slope. These two distinct ultrasound generation regions suggest that there are two different types of probe-sample interactions. After the above measurements, the resonant frequency of the free TF was unchanged.

Figure 5A:
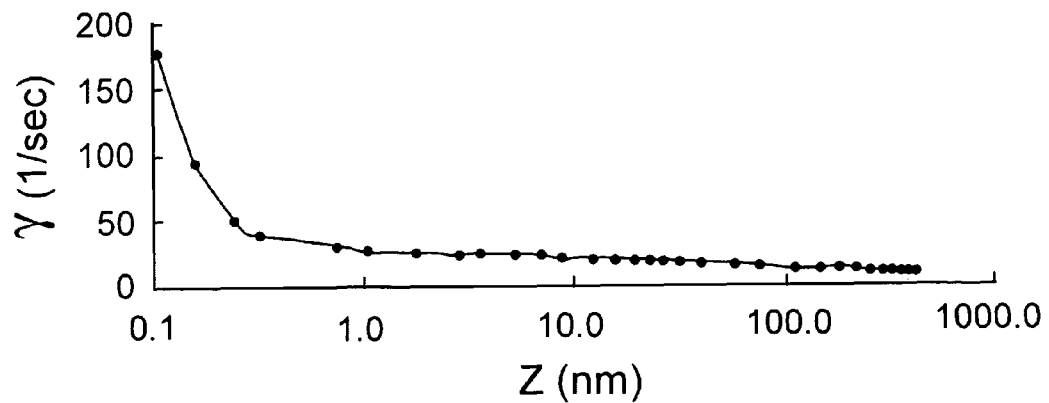
FIGS. 5A-5C are graphs of a damping constant, a force gradient, and ultrasonic signal magnitudes as functions of probe tip/specimen separation, respectively.
Figure 5B:
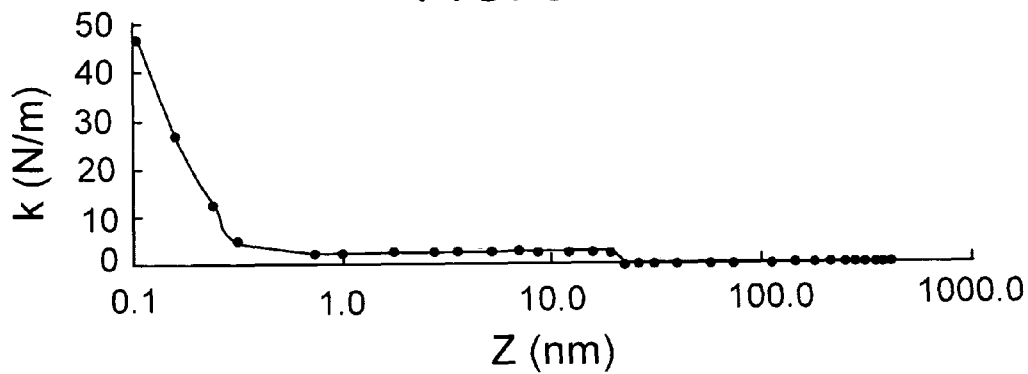
Figure 5C:
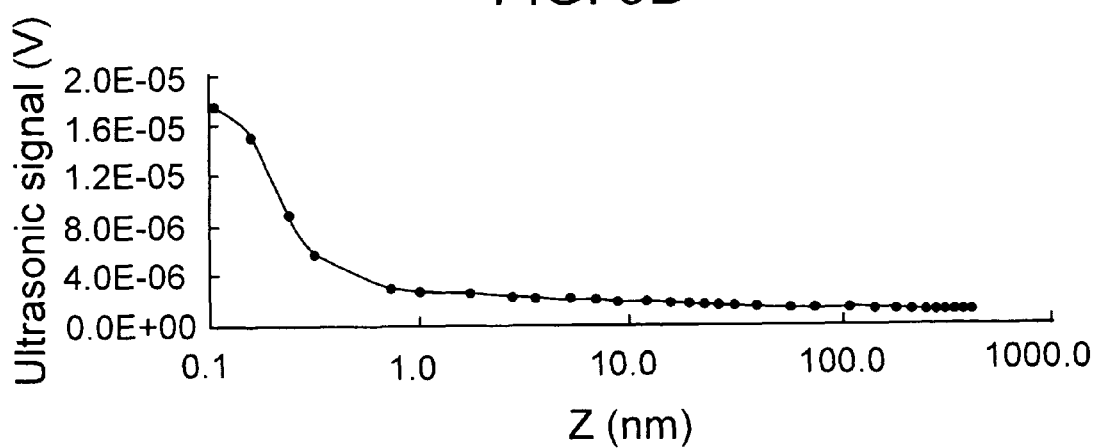

FIGS. 5A-5C illustrate effective damping rate, force gradient, and ultrasonic signal change as a function of probe-specimen distance z at a 60 mV tuning fork drive voltage. The probe-specimen separation at which distortion of the TF admittance spectrum is observed is taken to be the sample surface (i.e., z=0 nm).

There are two different regions of the probe-sample interaction can be observed in FIGS. 5A-5C. When the probe is several hundred nanometers away from the sample, the damping rate increases linearly as the probe-sample distance z decreases. The force gradient and the ultrasonic signal do not change appreciably. The probe-sample interaction in this region is largely dissipative and there is no reactive interaction involved. The presence of a contamination layer (water or hydrocarbon compound layer) accounts for the viscous dissipation, because the viscous force due to the air layer between the probe and the sample is very small, on the order of $10^{-13} \sim 10^{-15}$ N. When the probe-sample distance is less than 1 nm, the damping rate of the TF, the force gradient, and the ultrasonic signal increase dramatically.

Figure 6A:
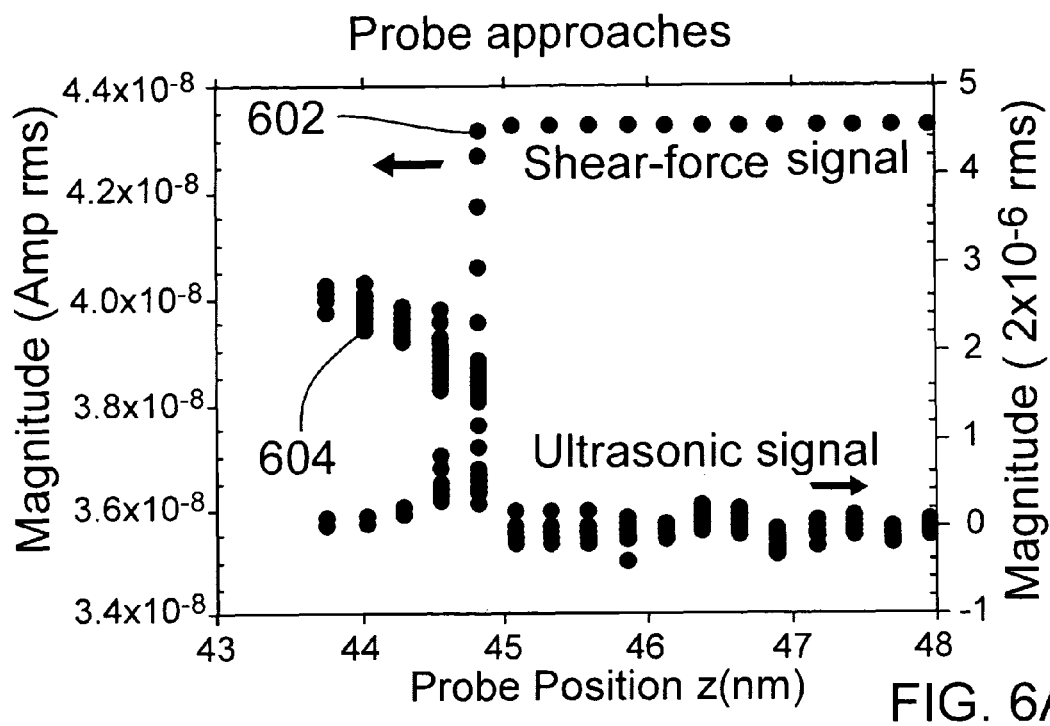
FIGS. 6A-6B are graphs illustrating shear force and ultrasonic signal amplitudes as functions of probe-specimen displacement for a probe that is moved so as to approach a specimen (FIG. 6A) or for a probe that is retracted from a specimen (FIG. 6B).
Figure 6B:
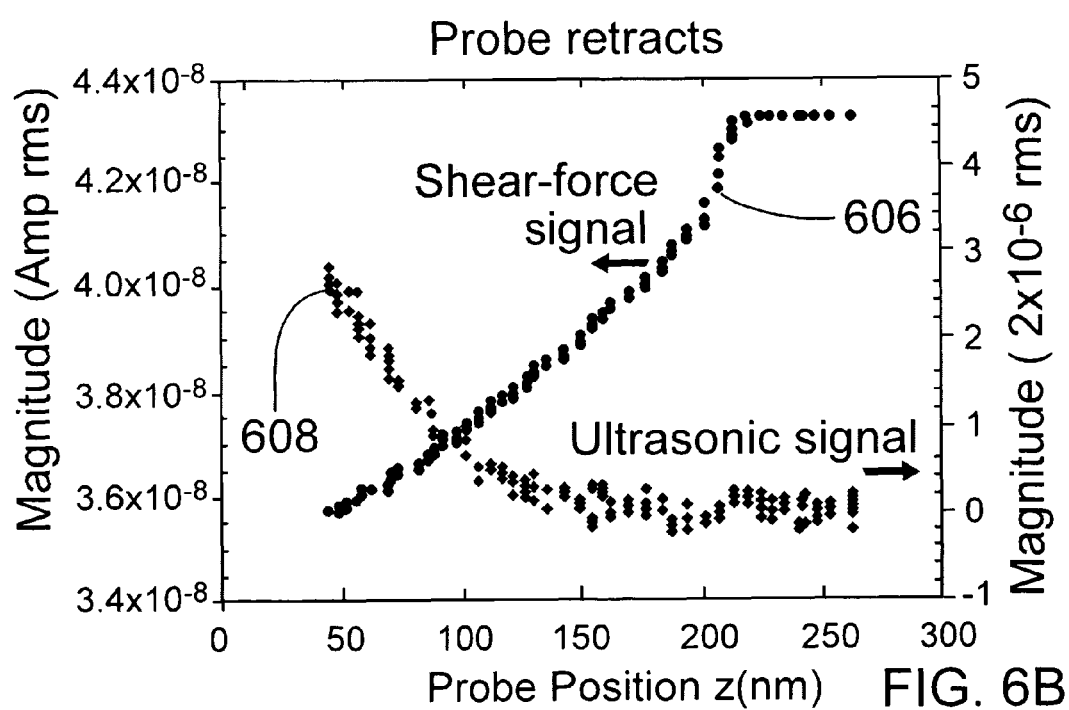

FIGS. 6A-6B illustrate signals obtained with the tuning fork 104 and the ultrasonic transducer 120 as the probe tip 103 is moved towards or away from the specimen surface 117. In FIG. 6A, as the probe tip approaches the specimen surface 117 (i.e., as z is decreased), a shear force signal 602 decreases abruptly (at a relative displacement z of about 44.8 μm), indicating that the probe tip is contacting the specimen surface 112. The ultrasonic signal also changes abruptly. After reaching the position at which the tuning fork 104 is indicated as contacting the specimen 114, both the tuning fork signal and the ultrasonic signal remain relatively constant with respect to further tuning fork displacements towards the specimen. Thus, FIG. 6A shows that the approach of the probe tip 103 to the specimen can be detected so as to anticipate subsequent probe contact, providing a sensitive indicator for use in probe positioning. In addition, the ultrasonic signal is associated with interaction of the probe tip and a fluid layer on the specimen.

Referring to FIG. 6B, as the probe tip is withdrawn from the specimen (i.e, as z is increased), a tuning fork signal 606 (a shear force signal) changes somewhat gradually until the relative displacement z is about 210 nm. At this displacement, the tuning fork signal 606 increases abruptly. In contrast, an ultrasonic transducer signal 608 exhibits a noticeable change only at a displacement of about z=150 nm, and does not exhibit an abrupt signal behavior expected for the transition from probe contact to noncontact.

Referring to FIG. 7, a TF signal magnitude and ultrasonic sensor signal magnitudes are graphed as a function of time as a probe tip is moved towards and away from a glass sample. The probe tip is advanced toward the specimen in an interval 701 in which both signals remain substantially constant until a layer boundary is reached near the end of the interval 701. At this displacement, the TF signal decreases and the ultrasonic signal increases. The observed increased intensity of the ultrasonic signal as specimen/probe tip distance is reduced can be ascribed to a distance dependence of the adsorbed layer's viscoelastic properties, but this explanation may require that a viscoelastic coefficient for a water film (the adsorbed layer) that is much larger than a value for a bulk sample. A high viscoelasticity of the adsorbed layer acts can serve as an amplifier of acoustic waves generated by a laterally oscillating probe tip. During an interval 703, the probe is moved both toward and away from the specimen, and increases in the TF signal are associated with decreases in the ultrasonic signal. During this interval, the probe appears to be in contact with an adsorbed surface layer. In an interval 705, the probe tip is gradually retrieved from the surface (so that there is no hard contact between the probe tip and the specimen surface), but a clear ultrasonic signal is detected, demonstrating that an ultrasonic signal can be generated in the adsorbed layer. Finally, during an interval 707, the probe tip is moved toward and away from the specimen in a manner similar to that of the interval 703, but at a greater distance. Amplitude changes in the TF signal produce smaller changes in the ultrasonic signal than in the interval 703.

The "negative" correlation between the TF and ultrasonic signals (that is, one decreases while the other increases, and vice versa), is a common behavior observed with different types of samples such as glass, atomically flat mica, silicon wafers, and stainless steel, with thicknesses from less than about 1 mm up to about 5 mm. In some cases, however, a positive correlation is observed.

Figure 8A:
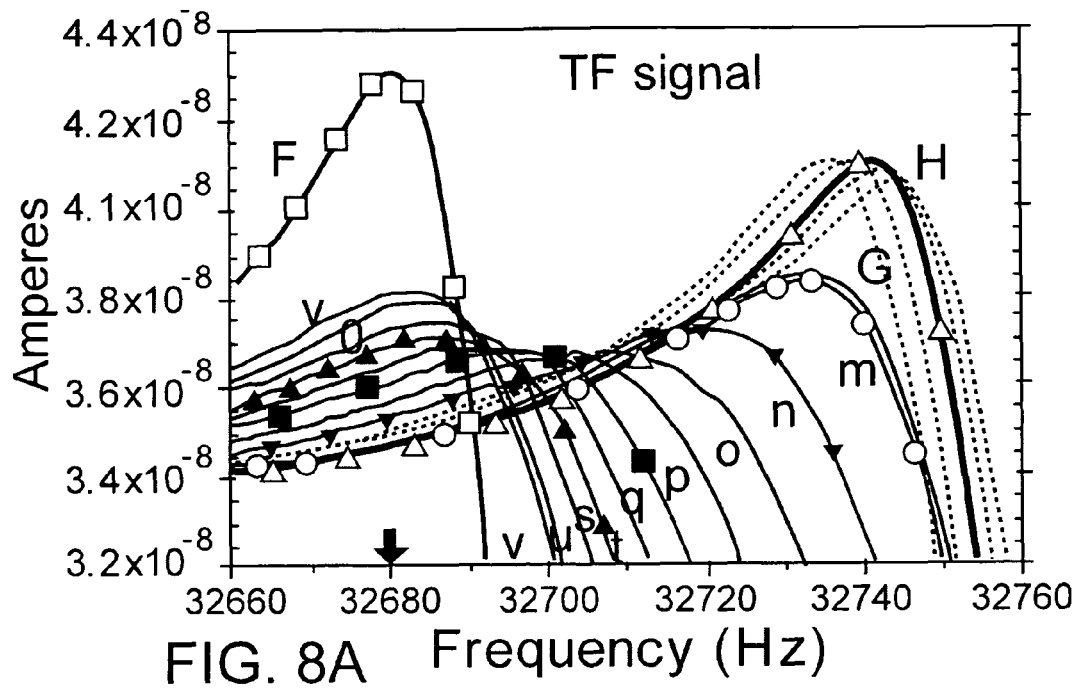
FIGS. 8A-8B are graphs of a tuning fork signal and an ultrasonic sensor signal as functions of frequency for various probe tip/specimen separations.
Figure 8B:
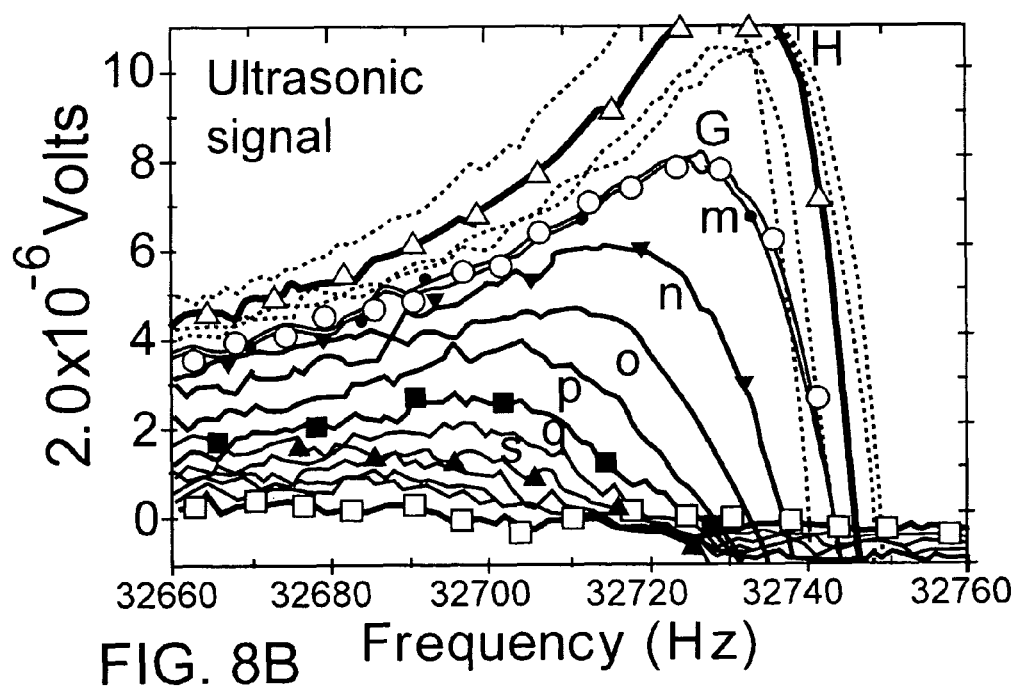
Figure 9A:
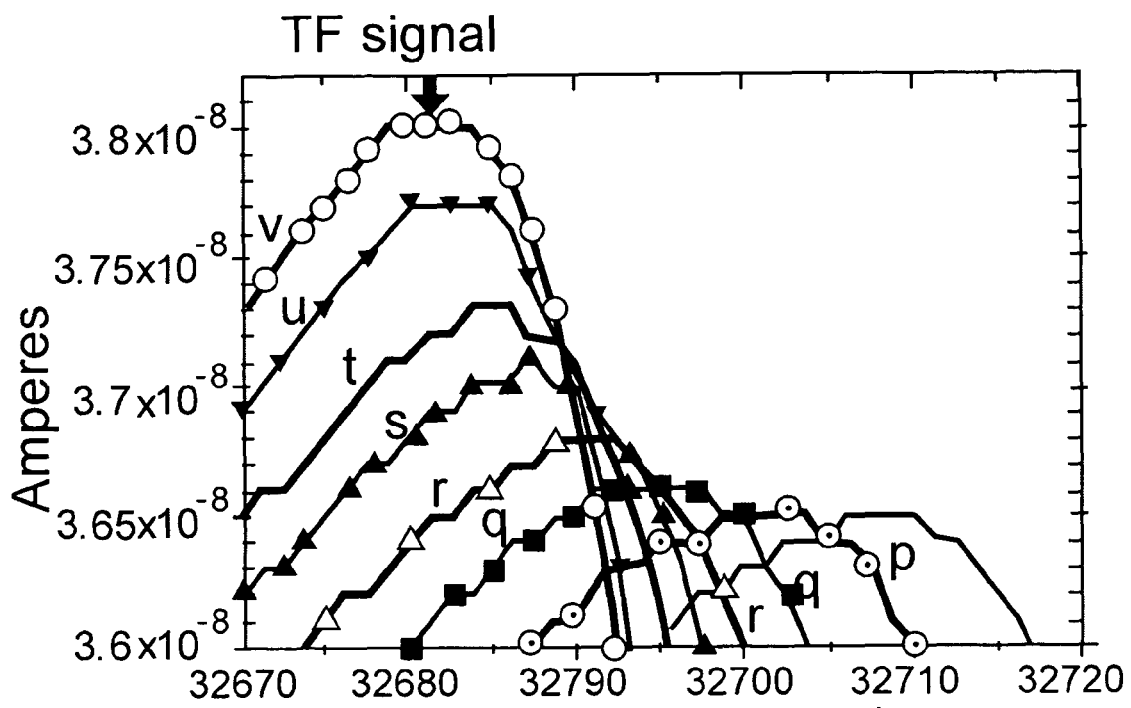
FIGS. 9A-9B are enlarged portions of the graphs of FIGS. 8A-8B.
Figure 9B:
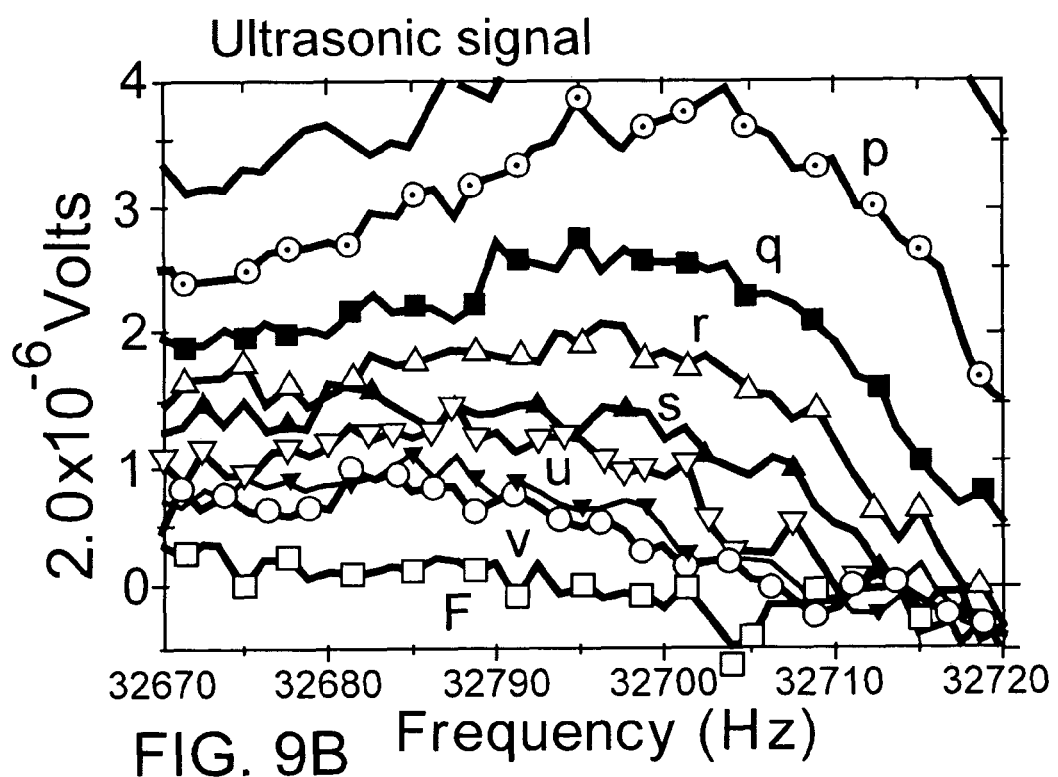

FIGS. 8A-9B illustrate representative measurements that include signals from the tuning fork and the ultrasonic sensor. FIGS. 9A-9B represent enlarged portions of FIGS. 8A-8B. FIG. 8A shows tuning fork signal spectra taken at different probe-sample distances, starting with the probe tip positioned distant from the sample (curve F), while approaching the sample (curves G and H), and during a gradual retraction (curves m to v, in alphabetic order). Corresponding ultrasonic signals are shown in FIG. 9A. The TF signals shown in FIG. 9A are based on a magnitude of an rms value of an ac current supplied by the TF and the ultrasonic signal is associated with an output of the ultrasonic transducer as processed by a lock-in amplifier. During the approach of the probe tip to the specimen, it can be difficult to acquire stable spectra just after the probe encounters an adsorbed layer. In FIGS. 9A-9B. curve G corresponds to a probe tip immersed into the adsorbed (contamination) layer, and likely in contact with a surface of the specimen. Moving the probe tip further toward the specimen (curve H) causes a further increase of the TF signal rather than a signal decrease that would be expected if the probe tip were immersed only in the adsorbed layer.

After the probe tip appears to have contacted a solid surface (curve H), further movement of the probe tip to the sample does not generally produce an increase in TF signal amplitude. In addition, slightly different z-axis control voltages produce frequency response curves (shown as dashed lines) situated about the curve H without appreciable resonance frequency shifts. Thus, the probe tip signal appears to correspond to clamping of the probe tip to the sample. However, even with the probe tip clamped in this manner, ultrasonic signal magnitude can vary considerably as can be noted in the dashed line curves of FIG. 8B.

The TF signal exhibits different behaviors for displacements on either side of a displacement associated with curve q, and, for convenience, the curve q displacement can be defined as a z=0 reference as a displacement at which the probe tip stops making solid-solid contact with the specimen surface during retraction. A frequency shift of 15 Hz in the ultrasonic signal is observed between spectrum q and spectrum v (an additional probe tip retraction of about 80 nm). Notice also that the intensity of the ultrasonic signal varies with the frequency shift; the greater the resonant frequency shift, the greater the ultrasonic signal Thus, the adsorbed layer is associated with both a damping force and an elastic restoring force.

Scanning probe microscopes that sense acoustic or ultrasonic signals in a specimen such as described above are well suited for analysis and evaluation of a wide variety of specimens. For example, nanofluid channels or devices can be characterized. Coupling and propagation of acoustic waves into the specimen by a scanning probe tip can be used to investigate subsurface specimen properties, such as cavities configured as nanofluid channels.

In view of the many possible embodiments to which the principles of the disclosed technology may be applied, it should be recognized that the illustrated embodiments are only preferred examples and should not be taken as limiting the scope of the technology. For example, various types of acoustic transducers can be used to apply and/or detect acoustic or ultrasonic signals. Piezo-electric transducers are convenient. These transducers can be configured as resonant mechanical structures such as tuning forks or other acoustic resonators. Alternatively, a driver or detection circuit can be coupled with an acoustic transducer to produce a resonant device based on the transducer/circuit combination. Detected signals can be processed with narrowband, phase sensitive circuitry, or frequency shifts, changes is admittance spectra, or changes in Q can be otherwise detected. For convenience, piezo-electric transducers in stage translators used to position the probe tip to contact a specimen or for scanning in image formation can be used to detect or apply acoustic signals as well.

As described in the above examples, an ultrasonic transducer is configured to detect acoustic signals produced by an oscillating tuning fork. In other examples, the ultrasonic transducer can be used to produce an acoustic wave or other acoustic vibration that is coupled to a probe configuration such as that of FIG. 1. In addition, one or more ultrasonic transducers can be situated on an upper surface (such as the surface 119) of a specimen, or secured to a translation stage used to position either the probe or the specimen. A transducer can be acoustically coupled to the same side of the specimen contacted by the probe tip. Several such transducers can be used to apply acoustic signals, or to detect acoustic signals for assessing probe location or for use in image formation. Acoustic transducers are generally located so as to be acoustically coupled to a probe tip, wherein the coupling is a function of probe/specimen displacement.

Figure 10:
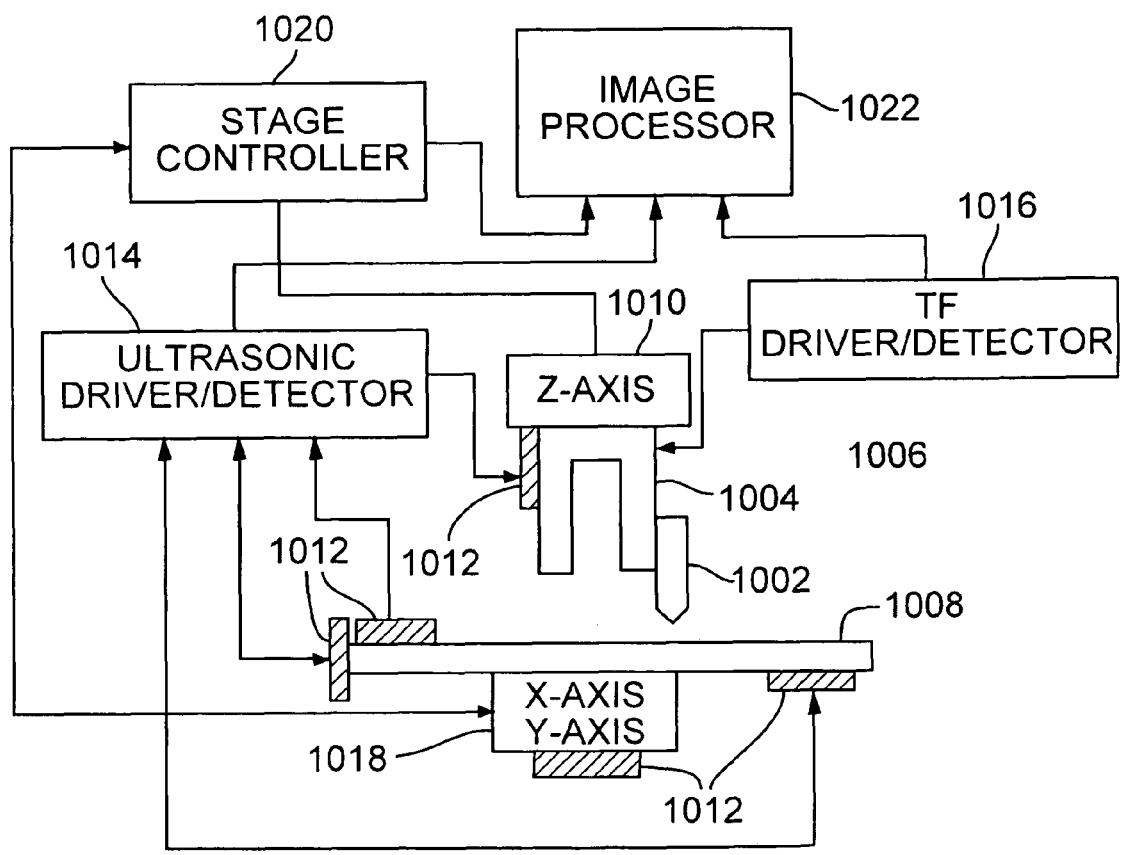
FIG. 10 is a schematic diagram of a scanning probe microscope that illustrates placement of ultrasonic transducers.

An additional representative example is illustrated in FIG. 10. A probe 1002 is coupled to a tuning fork 1004 that is configured to be moved toward or away from a specimen 1008 with a z-axis stage 1010. Ultrasonic transducers 1012 are provided at a variety of locations, and are coupled to a driver/detector 1014 so that one or more of the ultrasonic transducers can be used to produce or detect acoustic waves. A TF driver/detector 1016 is similarly configured to produce or detect acoustic waves. The specimen 1008 can be scanned with an XY-stage 1018 under the control of a stage controller 1020. Detected signals and position data from the stage controller 1020 are delivered to an image processor 1022 that produces specimen images. Typically, the ultrasonic transducers are piezoelectric devices, but other acoustic generators/detectors can be used. In addition, as shown in FIG. 10, the tuning fork 1004 is oriented to that the probe tip oscillates substantially laterally with respect to the specimen surface. In other examples, the tuning fork can be tilted with respect to the sample surface to have a substantial vertical oscillation component to "tap" on the sample surface.

So-called Whispering-Gallery Remote Ultrasonic-Sensing (WGRUS) provides a novel, simple, low cost, and non-invasive acoustic detection technique for controlling probe vertical position in SPM. In representative examples, a WGRUS-based SPM uses a tapered stylus attached to one of the tines of an electrically driven piezoelectric tuning fork (TF), capitalizing on the sensitivity of the TF tine lateral motion to the distance between the sample surface and the stylus tip. This lateral motion also produces mechanical vibrations on the microscope stage, which can be detected with high sensitivity based on whispering gallery modes. A convenient approach adopted in the WGRUS SPM consists of properly designing (according to probe oscillation frequency) a cylindrical stage that favors the establishment of standing ultrasonic whispering-gallery waves, allowing monitoring of the mechanical waves very efficiently with an ultrasonic transducer placed in contact with the cavity. Changes in the magnitude and phase of the ultrasonic waves (due to the distance-dependent interaction between the probe tip and the sample) are thus detected with high sensitivity by the ultrasonic transducer, whose output signal can be used by a feedback electronic circuit to adjust the $V_z$ voltage of the sample z-positioning actuator in order to maintain a preset tip-sample distance (indicated by a set point input 1130 in FIG. 11A). As the probe is scanned laterally, the WGRUS allows an automated adjustment of the probe vertical position in such a way as to avoid tip crashes against potential unevenness in sample surfaces. Plotting the required $V_z$ voltage adjustment as a function of the (x,y) coordinates of the probe represents, after a proper calibration, the sample surface topography. One advantage of the WGRUS is its whispering-gallery mode detection strategy (or other resonance enhanced detection strategies) to control probe-sample distance.

WGRUS methods and apparatus can be simple and inexpensive to implement. For example, sophisticated high-cost optical alignment is not needed to monitor probe position as in conventional atomic force microscopy. Instead, simply attaching an ultrasonic transducer and a resonant cavity around a SPM microscope is sufficient for WGRUS implementation. Unlike conventional methods, WGRUS-based methods are substantially free of electrical interference. For example, in tuning-fork-based methods parasitic capacitance from external connections compromises finding TF mechanical resonant frequencies. The WGRUS resonant cavity can be located well away from the tip-sample interaction region, reducing the effect that the sensing measurement setup can cause on the surface interactions under study. Further, since the structure of the microscope itself can be designed with the proper dimensions as to act as a resonant cavity, the integration of the WGRUS sensing system can provide a compact microscope.

In a representative example, a WGRUS SPM uses glass fibers (3M FS-SC-6324; 120 μm cladding diameter) to form a probe tip using chemical etching procedures. Typical apex-radii of the tips range from 30 nm to 100 nm, with a tapered region of approximately 200 μm in length. A representative probe tip is illustrated in FIG. 12. Other types of probes, such as those configured for a near-field optical microscope can also be used.

A representative SPM 1100 that includes WGRUS is illustrated in FIGS. 11A-11B. An AC signal generator 1102 is coupled to a piezoelectric transducer 1106 that produces periodic variations in position of a probe tip 1108. The probe tip 1108 is typically a tapered fiber and the transducer 1106 is a piezoelectric tuning fork (TF) of nominal resonant frequency (32 kHz) prior to attaching the tapered fiber probe tip. The signal generator 1102 typically produces ac-voltage amplitudes ranging from about 4 mV to about 50 mV rms, and probe tip oscillation amplitude is between about 1-5 nm depending on tuning fork Q after probe tip attachment (Q typically between 300 and 2,500). The probe tip 1108 is situated at or on a specimen 1116 that is supported by an XYZ actuator 1112 and a stand 1114.

A cylindrical dome 1104 is configured to provide a WGRUS cavity or other path for standing whispering-gallery modes that propagate along an axis 1115. Lateral oscillations of the TF also become the source of ultrasonic waves that propagate upwards towards the cylindrical dome 1104. In an example, the whispering gallery propagation path is defined in stainless steel (longitudinal sound wave speed $v_{steel} \sim 5{,}000$ m/s), and a cylindrical dome of 158 mm perimeter is used to establish waves of $\lambda_{sound} \sim (5{,}000 \text{ m/s})/(32{,}000 \text{ Hz}) = 156$ mm, wherein the exact value depends on the exact frequency at which the TF is driven. The standing waves are detected with an ultrasonic transducer 1110 attached externally to the lateral wall of the cylindrical dome 1104. At some specific locations, the transducer 1110 detects comparatively high signal levels, corresponding to whispering-gallery modes in the cylindrical dome 1104. The output of the ultrasonic transducer 1110 is coupled to lock-in amplifier and other control or detection components. Typically, the amplitude and phase of the whispering gallery ultrasonic waves relative to the driving reference signal from the signal generator 1102 are detected.

Figure 13:
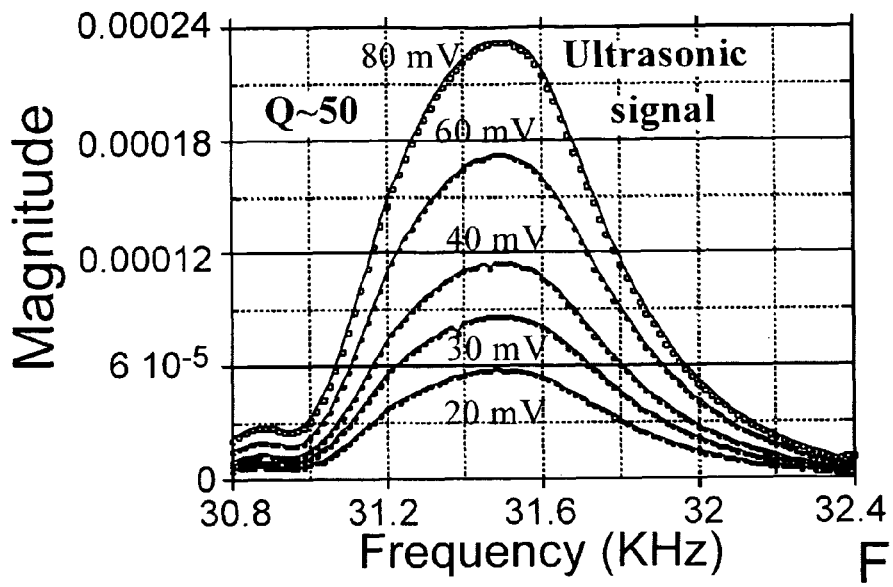
FIG. 13 is a graph of WGRUS cavity frequency response.

Good mechanical coupling between the TF holder and the resonant cavity dome is convenient and the resonant frequency of the combined TF/probe should be close to the 31.5 kHz at which the resonant cavity peaks. To estimate the quality factor of the cavity resonator, in one example implementation, a piezo plate was attached to the base of the cavity in order to shake the cavity at different frequencies and different amplitudes. The frequency response of the cavity is shown in FIG. 13. Note that the amplitude of the resonance peak varies with the applied driving voltage of the piezo-plate shaker (thus verifying the mechanical nature of this resonant peak). In the range of voltages tested, the amplitude peak varies linearly with the applied voltage. With a 0.6 kHz bandwidth at half-max, the resultant quality factor of the cavity is ~50.

Figure 14A:
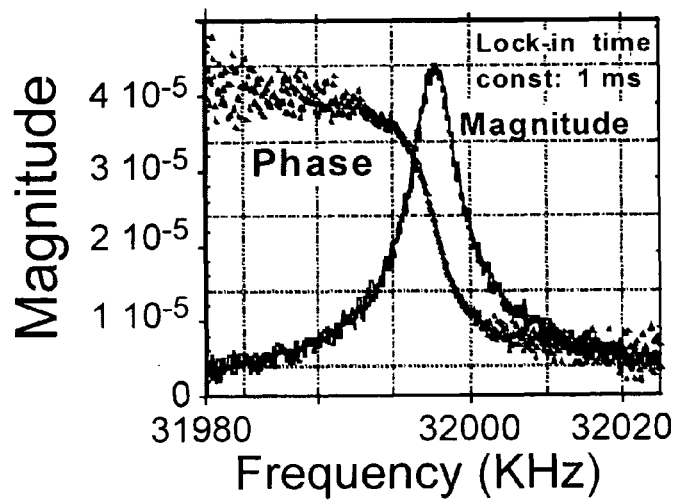
FIGS. 14A-14B are representative graphs of magnitude and phase of mechanical frequency-response of the electrically driven piezoelectric element monitored with the ultrasonic signal. The magnitude and phase response were taken while keeping the probe far away from the sample. Lock-in synchronous detection allows detection with time constant less than 3 ms, as shown in the left (1 ms) and right (3 ms) figures above. Drive voltage was about 50 mV.
Figure 14B:
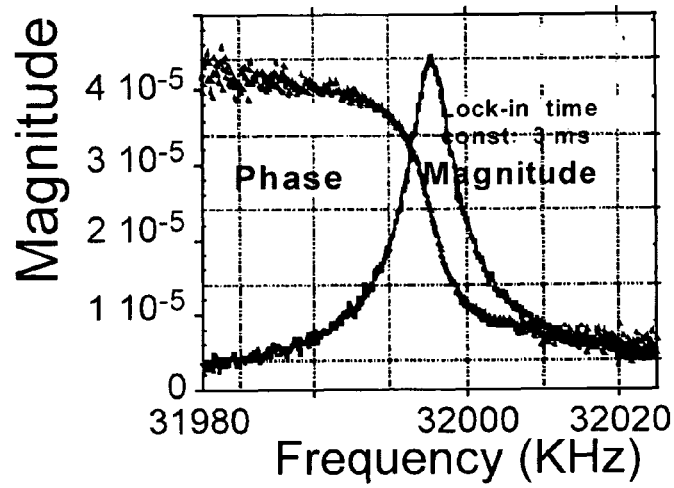

In a typical application, the WGRUS system is used first to characterize the frequency response of the piezoelectric TF that produces the ultrasonic waves. The sensitivity of the WGRUS cavity is sufficient to operate under typical conditions as used in other proximal probe microscopes (i.e. probe oscillation amplitudes of the order of nanometers, and synchronous detection with time constants less than 3 ms, as demonstrated by the spectra displayed in FIGS. 14A-14B).

Figure 15:
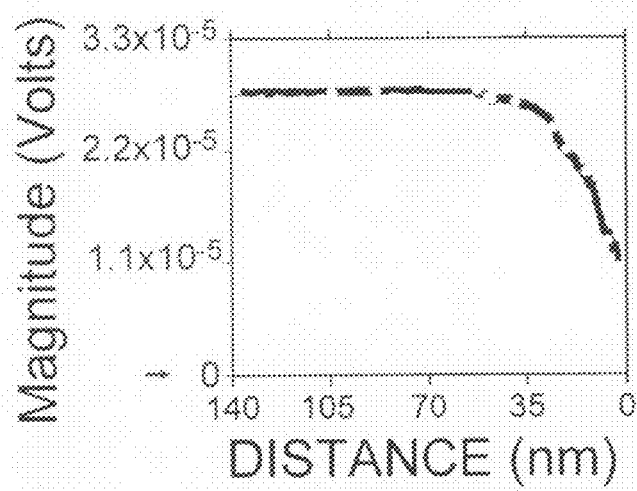
FIG. 15 illustrates variation of the ultrasonic signal as the probe approaches the sample surface (from left to right in the figure). The surface is nominally located at z=0. For comparison, the variation of the tuning fork (TF) signal is indicated with open circles.

The control of the probe vertical position in SPM is based on interactions between the probe tip and the sample. In WGRUS, variations of the probe amplitude of vibration is sensed by the corresponding variations of the ultrasonic signal. The WGRUS probe tip is first moved towards the sample while being driven at its resonance frequency (measured when the tip is far way). Starting at a 5 µm tip-sample distance, no change is initially observed in the detected ultrasonic signal during the approach. But, when the tip is very close to the sample, a decrease in the ultrasonic signal is observed in the last 40 nm, as shown in FIG. 15. The decrease in the probe oscillation amplitude is typically attributed to the presence of a thin contamination layer (water and hydrocarbons) present on the surface of any sample at ambient conditions. The sample solid surface is nominally located at z=0. For comparison purposes, the electrical response of the piezoelectric element (a tuning fork in this case) is also displayed (trace with solid spheres).

The monotonic decrease in the ultrasonic signal with distance can be exploited to implement feedback control. As an example, consider the result displayed in FIG. 15 at a signal level of $2.2 \times 10^{-5}$ V as the set point value that the WGRUS system needs to keep constant while the tip is laterally scanned. This requires moving the probe tip vertically up and down according to the topographic features on the surface to avoid crashing the tip into the specimen. The $V_z$ voltage that is applied to the piezo and controls the vertical motion of the sample so as to maintain a constant ultrasonic signal level during the lateral scanning constitutes the information sufficient to reconstruct sample topography.

Figure 16A:
FIGS. 16A-16B are representative topographic images obtained with a WGRUS scanning microscope. The scale bar in the right image is 5 μm.
Figure 16B:
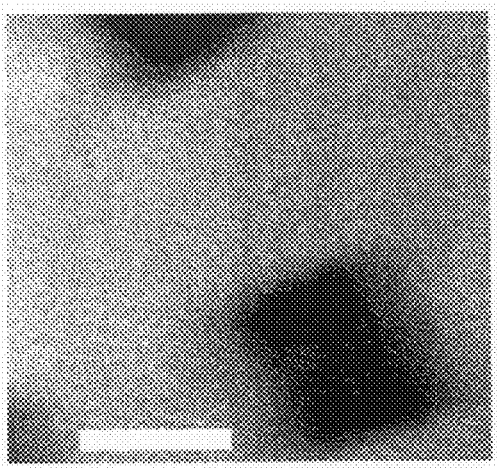

WGRUS makes the imaging task simpler, lowers the cost of implementing the mechanism for controlling the probe-sample distance, and is non-invasive. The imaging capability is demonstrated in FIGS. 16A-16B. The sample imaged is a micro-fabricated standard silicon sample that has a 200 nm thick thermally grown silicon oxide layer except at selected regions (squares of 5 microns side). Notice that the regularly arranged topographic depressions are well imaged (dark regions in the figure). The images were acquired using a 1 ms time constant in the lock-in amplifier setting, and at a scanning speed of 0.2 lines/s. The probe had a mechanical quality factor of Q=1000, and the applied ac driving voltage was 80 mV rms in amplitude.

Figure 17:
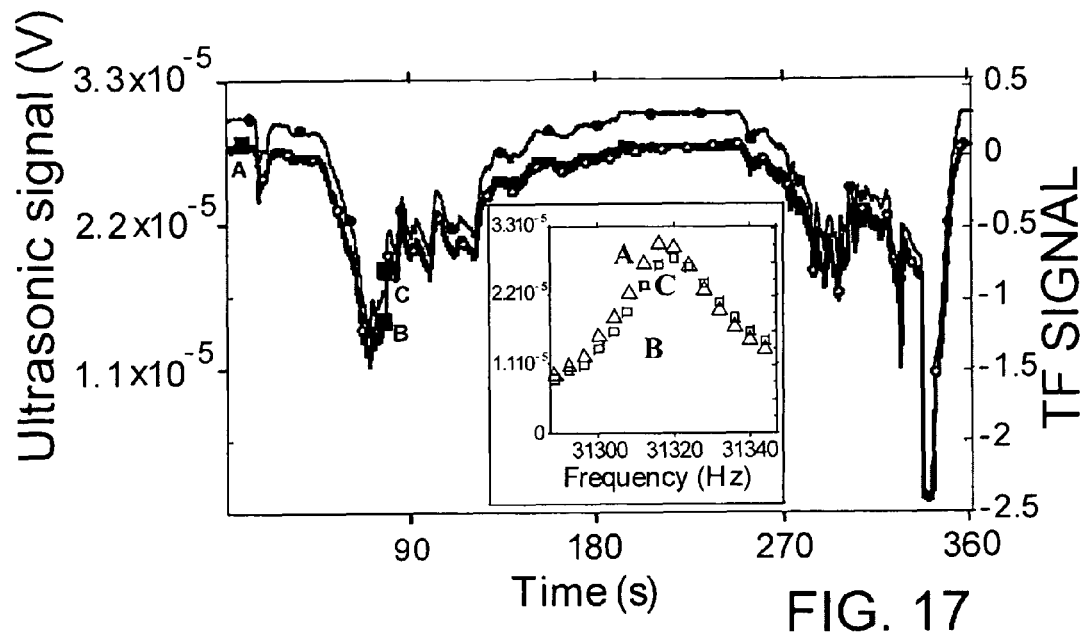
FIG. 17 illustrates demonstrated sensitivity of the WGRUS microscope to monitor probe-sample interactions. The trace with open circles displays the variations of the ultrasonic signal as the tip approaches and is retracted from a surface of a mica specimen (depicted in the inset diagram at the left). For comparison, the variation of the TF electrical admittance is also shown (filled circles). The inset at the center displays the resonant frequency of the probe taken at different instances during the approach.

WGRUS can also be used to study surface interactions in more detail. FIG. 17, for example, shows the variation of the ultrasonic signal (trace with open circles) as a function of time when the probe is forced (by the microscope user) to approach and retract from the surface while remaining inside the contamination layer. The instabilities displayed by the trace are not due to a poor microscope stage design but to interactions (including electrostatic interactions) between the tip and the surface. These solid-solid interactions are believed to be mediated by the mesoscopic fluid-like contamination layer. For example, this fluid-like film may be the reason for the increase in the probe's resonant frequency as the tip gets closer to the surface (as evidenced by the spectra displayed in the inset).

Another advantage of WGRUS over other SPM techniques that also monitor surface interactions based on the probe response is that the ultrasonic signal provides more reliable information about the state of the tip mechanical motion. Indeed, higher oscillation amplitudes produce a stronger ultrasonic signal, while a zero ultrasonic signal level will indicate a zero vibration amplitude. That is not the case, for example, when the electrical admittance response of the TF is used for which the "zero" level is unknown. The ultrasonic signal, however, provides a reliable zero level reference. This can be important if the user wants to determine, for example, under what conditions the oscillatory motion of the tip is brought to a complete rest (see the right side of the trace displayed in FIG. 17 above). Thus, the WGRUS can be a useful tool in nanotribology.

Figure 18:
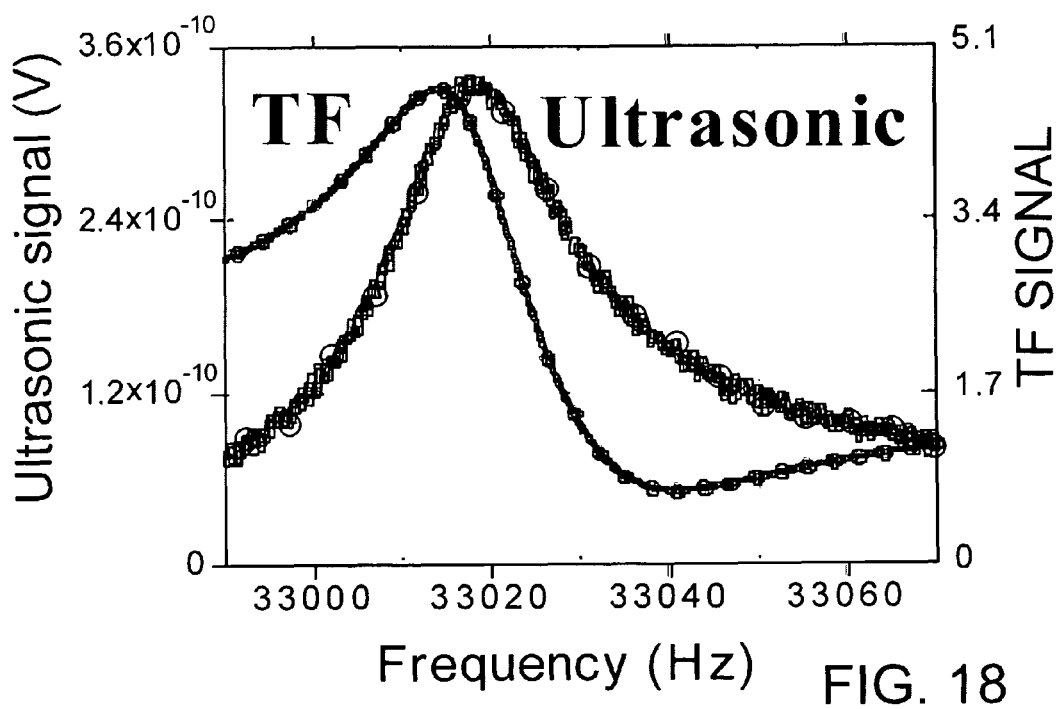
FIG. 18 illustrates a comparison between the ultrasonic (open circles) and TF admittance (filled circles) spectra. The peak of the TF signal does not coincide with probe mechanical resonant frequency, which is more reliably measured by the ultrasonic signal.

Similarly, the user may want to measure the exact mechanical resonance frequency. Again, due to the presence of external capacitance from the wiring connections, the peak of the TF admittance spectrum is not equal to the probe mechanical resonance frequency. The ultrasonic signal, on the other hand, is a direct measurement of probe mechanical motion. The peak of the ultrasonic signal measures more accurately the true mechanical resonance frequency. WGRUS renders a more reliable measurement as useful for metrology applications (see FIG. 18).

In other examples, mechanical (i.e., acoustic) contact between the TF holder and the member that connects the TF to the resonant cavity are provided. Relatively light materials having a high Young's modulus are preferred for a coupler to bridge the TF to the cavity resonator. Titanium is a good candidate. A metallic cover frame can be provided to reduced electrical noise from the surrounding environment. The microscope stage could be designed in a conical type shape (as opposed to its current cylindrical shape.) Such a geometry would allow a range of potential whispering-gallery modes that could be established in the cavity (that is, perimeters of different lengths would become available). This would be beneficial since the exact operating frequency of the WGRUS ultrasonic sensor depends on the somewhat unpredictable resonant frequency of the TF with an attached probe tip.

A WGRUS configuration can also be used with a Near-field Scanning Optical Microscope (NSOM) or other scanning microscopes to estimate probe/specimen distances so that microscope users can accurately location probe tips or so that probe tip/specimen displacement can be established with a control system based on the WGRUS acoustic signal.

In some examples, resonance enhanced acoustic signals can be obtained by locating an acoustic sensor at, for example, a preferred location in a cylindrical cavity such as that defined by a scanning microscope frame. At such a preferred location, acoustic signals can be as much as 80-100 times larger that in other locations.

Figure 19:
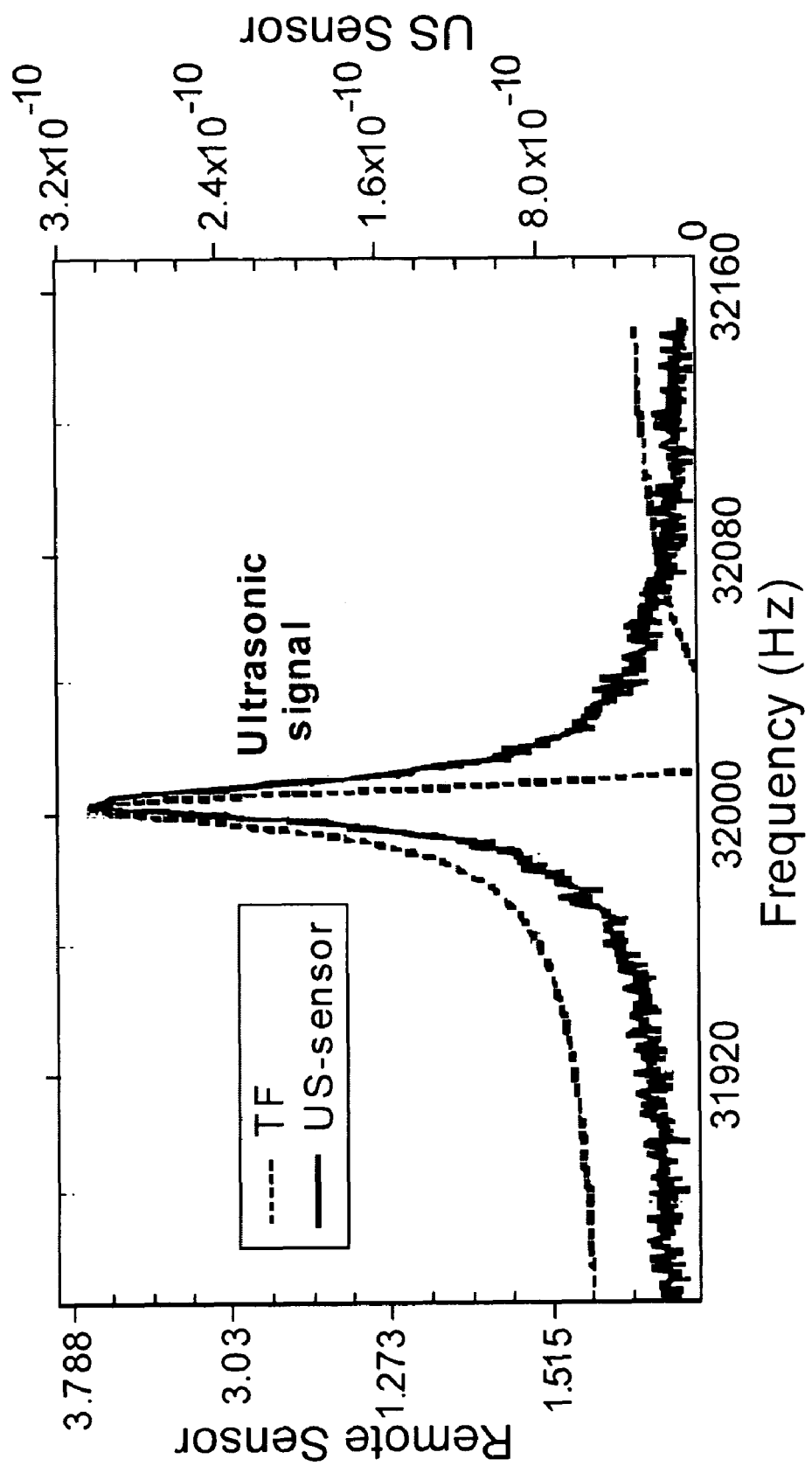
FIG. 19 is a graph illustrating tuning fork and ultrasonic signal spectra.

The spectrum of FIG. 19 were taken with a different scanner head-stage. The solid trace is the response from the remote ultrasonic sensor to (25 nm) lateral vibrations of the probe located at the heart of the microscope. The dashed trace is the response of the tuning fork sensor (electrical admittance), recorded simultaneously for comparison purposes. One application is for feedback control of probe vertical position in scanning probe microscopes.

Whispering-Gallery Remote Ultrasonic-Sensing (WGRUS) provides a simple, cost-effective method in scanning probe microscopy. Situating a sensor so as to receive an acoustic signal associated with an acoustic resonance permits estimation of probe tip/specimen displacements. Such a sensor can provide a signal associated with a direct measurement of probe motion of the probe, and it is unnecessary to evaluate TF admittance spectra.

While WGRUS can be convenient, enhanced acoustic signals can be detected based on other acoustic resonators. For example, an acoustic sensor can be coupled to a resonator structure defined as rod, cylinder, cone, ring, tuning fork, or other structure. Some resonator structures are defined as solid members to obtain reduced acoustic wavelength. Resonator Q can be selected so a change in probe tip resonance frequency such as that associated with probe tip replacement can be accommodated. These acoustic sensors can be situated remote from the probe tip/specimen interaction region.

The disclosed examples are not to be taken as limiting, and we claim as our invention all that comes within the scope and spirit of the appended claims.

We claim:

1. A scanning microscope, comprising:
 a probe having a probe tip for contacting a specimen;
 a stage configured to provide a selected probe tip-specimen displacement;
 a first acoustic transducer coupled to the probe;
 a resonant cavity acoustically coupled to the probe tip;
 a second acoustic transducer acoustically coupled to detect acoustic waves in the resonant cavity; and
 a first transducer driver configured to produce an acoustic vibration of the probe tip with the first acoustic transducer at a probe tip frequency, wherein the resonant cavity dimensions are based on the probe tip frequency.

2. The scanning probe microscope of claim 1, further comprising:
 a translation stage configured for scanning that the probe tip with respect to a specimen surface; and
 an image processor configured to receive electrical signals from the second transducer associated with acoustic waves in the resonant cavity as the probe tip is scanned and to produce an image of a specimen surface based on the received electrical signals.

3. The scanning probe microscope of claim 2, further comprising a quartz tuning fork that includes the first acoustic transducer, wherein the probe tip is secured to a tine of the tuning fork.

4. A scanning microscope, comprising:
 a probe having a probe tip for contacting a specimen;
 a stage configured to provide a selected probe tip-specimen displacement;
 a first acoustic transducer coupled to the probe;
 a resonant cavity acoustically coupled to the probe tip;
 a second acoustic transducer acoustically coupled to detect acoustic waves in the resonant cavity, wherein the resonant cavity includes a cylindrical section having a diameter associated with a probe tip drive frequency.

5. The scanning probe microscope of claim 4, wherein the cylindrical section is metallic.

6. The scanning probe microscope of claim 4, wherein the second transducer is configured to detect probe tip vibration based on acoustic waves in the resonant cavity.

7. The scanning probe microscope of claim 4, further comprising a controller configured to adjust probe tip-specimen separation to maintain a predetermined acoustic wave magnitude in the resonant cavity.

8. The scanning probe microscope of claim 7, further comprising a memory configured to store the probe tip-specimen separation.

9. The scanning probe microscope of claim 7, further comprising a display configured to present a specimen image based on the adjusted probe tip-specimen separations.

10. The scanning probe microscope of claim 9, wherein the predetermined acoustic wave magnitude is a constant magnitude.

* * * * *